Figure 1:
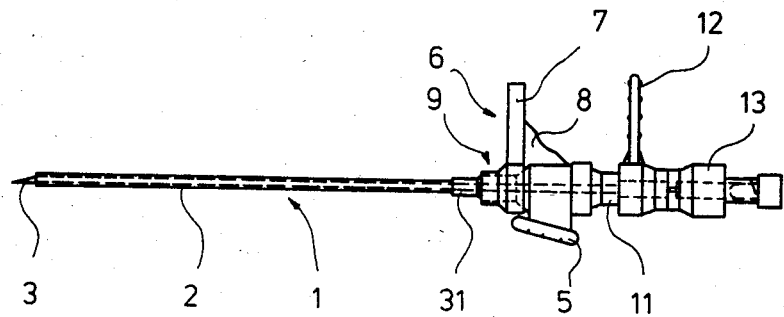

United States Patent [19]

Müller et al.

[11] Patent Number: 4,565,544
[45] Date of Patent: Jan. 21, 1986

[54] DEVICE FOR INTRODUCING A CATHETER

[75] Inventors: Franz-Josef Müller, St. Wendel; Viktor Krütten, Idstein; Gerd Krick, Bad Homburg, all of Fed. Rep. of Germany

[73] Assignee: Fresenius AG, Bad Homburg, Fed. Rep. of Germany

[21] Appl. No.: 579,210

[22] Filed: Feb. 10, 1984

[30] Foreign Application Priority Data

Feb. 12, 1983 [DE] Fed. Rep. of Germany ....... 3304914

[51] Int. Cl.⁴ .............................................. A61M 5/00
[52] U.S. Cl. .................................................. 604/164
[58] Field of Search ............... 604/164, 165, 166, 167, 604/168, 169, 174, 177; 128/DIG. 26

[56] References Cited

U.S. PATENT DOCUMENTS 3,537,451 11/1970 Beck et al. ........................... 604/165
4,191,186 3/1980 Keeler ................................. 604/164
4,209,015 6/1980 Wicks .................................. 604/164
4,451,256 5/1984 Weikl et al. ......................... 604/164

FOREIGN PATENT DOCUMENTS 0045849 2/1982 European Pat. Off. ............ 604/164

Primary Examiner—G. L. Kaplan
Attorney, Agent, or Firm—Omri M. Behr

[57] ABSTRACT

Device for introducing a catheter which is suitable in particular for catheterizing the vena basilica, jugularis or subclavia and substantially comprises a puncture cannula (2), a bush (4) having a tubular continuation (31), securing plates or wings (5) and a connecting piece (11) and possibly a metal needle extension (13) which is equipped with grip plate (12) and securing means, a detachable extension piece (6) being fitted on the bush (4) and comprising substantially a grip plate (7), a hollow portion (9) having a slit (21, 29) and possibly a support member (8), the slit extending over the entire length of the extension hollow portion (9) either at the bottom side or laterally thereof.

23 Claims, 12 Drawing Figures

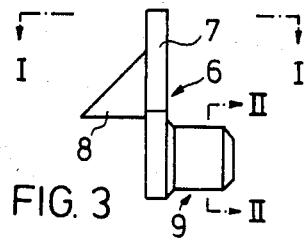
FIG. 3
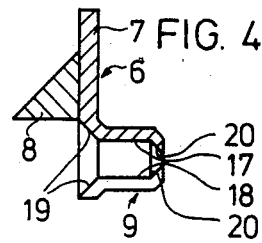
FIG. 4
FIG. 5
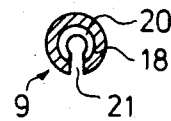
FIG. 6          FIG. 7
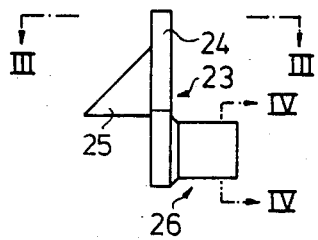
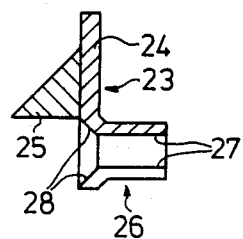
FIG. 8
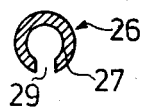
FIG. 9          FIG. 10
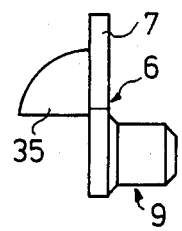
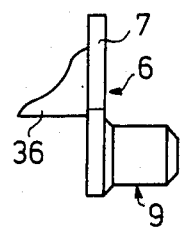

DEVICE FOR INTRODUCING A CATHETER

The invention relates to a device for introducing a catheter into body cavities and vessels in which a catheter tube and a puncture needle are disposed in a bush which comprises two substantially planar plates which when the bush is disposed on the skin of the patient bear directed towards two opposite sides on the skin, and in which the puncture needle comprises a grip piece and the bush comprises at least one grip plate.

As is known, in the continuous treatment of patients catheters can be used as vein short-time catheters of vein indwelling catheters with flexible catheter tube or with metal cannula or alternatively as introduction aid for a further catheter which is for example introduced by the first catheter into a body vessel.

Since catheters are usually made from highly flexible and histocompatible material, they are generally introduced into the body of the patient with a puncture needle of metal with beveled point. This puncture needle passes through the plastic puncture cannula or catheter tube in its entire length and projects from the other end of the puncture cannula or catheter tube only with the beveled tip. With this tip the skin and vessel wall is punctured and thereafter said needle is pushed together with the puncture cannula or catheter tube into the vessel. After the puncturing, the puncture needle is withdrawn and the laid catheter remains behind and advantageously has at its uninserted end corresponding connection and securing means and is sealed by a valve.

For puncturing a blood vessel it is necessary to use such a puncture needle which is pushed through the bush of the puncture cannula, and the metal cannula or needle hub, i.e. extension, may have a grip piece. As already explained, when the puncture has been effected the puncture needle is withdrawn from the puncture cannula and thereafter the catheter tube is pushed through the puncture cannula into the blood vessel. After a radiographic investigation of the catheter fit the puncture cannula is removed from the body, locked to the connection and securing means of the catheter and secured to the skin of the patient. For this purpose securing means directed away from the bush on opposite sides are used, such as fixing plates or wings, which after the puncture of the blood vessel lie on the skin of the patient and are adhered thereto by plaster or adhesive tape (DE-PS No. 2,609,112), or are sewn to the skin through openings (slots or holes) in the wing tips. These plates are fixedly and immovably connected via webs to each other and to the bush. Such an immovable arrangement of the plates also results when they are clamped with clips onto an extension of the catheter bush on the tube or metal cannula side (DE-GM No. 7,333,964).

Furthermore, a catheter is known having plates movable into two positions perpendicular to each other. The moveability is botained by flexible wings which for the puncturing are folded upwardly against each other about bending lines parallel to the longitudinal axis of the catheter and in this position serve as introduction aid (DE-OS No. 2,116,108, DE-OS No. 2,433,767). This arrangement is disadvantageous because on exerting the advancing force necessary for puncturing the fingers of the user can easily slip off the wings. If a metal needle with grip piece is additionally used said grip piece then extends transversely of the folded-up wings of the catheter. Consequently, the folded-up wings of the catheter cannot be gripped between thumb and index finger simultaneously with a grip piece of the cannula extension and for this reason when using this known catheter for puncturing only a metal needle without grip piece can be employed. This is disadvantageous because the metal cannula cannot be held firmly during the puncturing and can therefore shift in a longitudinal direction.

Another solution is proposed in DE-PS No. 2,929,886. In the latter, the two fixing plates on the catheter extension are rigid connected together via a strap member and mounted about a pivot axis transverse of the longitudinal axis of the catheter extension on the extension hollow portion or on the bush of the catheter. For the puncturing these plates can be correspondingly pivoted upwardly and employed by the user as puncturing aid, and when a metal cannula extension is used with grip piece said grip piece and the two pivoted-up plates can be gripped simultaneously by the user between thumb and index finger. However, this type of catheter or catheter extension has the disadvantage that the two plates are too elastic and movable with respect to the grip plate of the metal cannula extension, i.e. they are not sufficiently rigid and slip-resistant and consequently during the puncturing longitudinal shifting of the parts relatively to each other is not adequately prevented and a reliable puncture is not guaranteed. This is particularly disadvantageous when an extremely precise and reliable puncture is to be made as is necessary for example when catheterizing the upper vena cava. It is also disadvantageous that the plates must be relatively large in order to be used as fixing plates although such large plates are more of a hindrance than puncturing aid during the puncturing itself.

The problem underlying the invention is therefore to provide a device of the type outlined at the beginning which can be adequately and reliably secured and which permits a certain and reliable handling during the puncturing.

This problem is solved in that the grip plate is connected to an extension hollow portion which engages around the bush, comprises a longitudinal slit and is detachable from the bush. Preferably, the extension piece may have a support member and/or possibly at the surface of the bush a guide element for the support member and/or for the slit extension hollow portion.

The fact that the extension hollow portion is slit provides for fitting and removal of the extension piece whilst by the guide element preferably provided for the support member and/or the extension hollow portion on the bush the extension piece is fixed on the bush and a lateral turning or shifting of the extension piece on the catheter is avoided. The support member, which is secured to the actual grip plate of the extension piece and engages in the guide element (e.g. guide groove), like the guide element possibly advantageously present for the slit of the extension hollow piece, makes it impossible for the grip plate to move laterally or in the longitudinal direction of the catheter and because the slit extension hollow portion engages around the bush of the catheter an unintentional tearing off of the extension piece from the catheter is avoided, i.e. the grip plate is adequately rigid and thus permits certain and reliable handling during the puncturing. When using metal cannula extensions with grip piece for the puncturing the user can grip the grip plate of the extension piece and grip piece of the metal cannula extension simultaneously and reliably between thumb and index finger and during the puncturing the catheter can be pressed against the metal cannula extension so that longitudinal displacement of the parts relatively to each other is avoided and reliable handling is ensured.

The puncturing of blood vessels is facilitated and made more reliable and safer by the device according to the invention.

Moreover, after removal of the extension piece the device according to the invention can be kept together with said extension piece in compact manner in a flat package.

The catheter itself, to which according to the invention a detachable extension piece is fitted, corresponds to the catheters generally used in medical technology and comprises the usual securing elements and means. It comprises essentially a bush or sleeve to one end of which is secured a flexible catheter tube or flexible catheter rubber tubing and to the other end of which a connector is secured comprising the usual securing means for a supply line and the metal cannula extension, and possibly at least one securing element connected to the bush, for example a plate or two substantially planar plates or wings which are connected together and to the bush and which are secured to the skin of the patient and lie directed towards two opposite sides on the skin, and possibly metal (steel) cannula or needle hub or extension. This metal needle extension itself may carry a grip piece extending substantially perpendicularly to the metal cannula, is constructed like the metal cannula hubs or extensions generally employed in medical technology and also has the securing means generally usual in the art. This grip piece of the metal cannula extension may have various forms and comprise for example on one or both sides longitudinal grooves and/or transverse grooves and/or depressions for engagement by the fingers so that they can be held in slip-resistant manner.

To prevent body fluid emerging from the catheter in the opened condition or air entering the vein and causing embolisms, in the bush a valve can be disposed which can be opened by the tip of the metal cannula or of a Luer connecting cone. The catheter flexible tubing or tube is fixedly connected to said bush via a tubular extension thereof.

As already explained, the extension piece which can be attached and removed according to the invention comprises the actual grip plate, a slit extension hollow portion and possibly the support member. All the parts are fixedly connected together.

The grip plate itself may have any suitable shape and for example be round, oval rectangular, square, semicircular or the like. It is preferably made round or oval. The size is also not critical but is should not be so large or so small that it could impair reliable handling in puncturing. As regards size, form and shape it may correspond to the grip piece of the metal needle hub or extension or be different thereto. Expediently, it has the same form and shape as the grip piece of the metal needle extension and is so large that one or more fingers, preferably one or two fingers, in particular one finger, can be placed thereon. The surface of the grip plate may have different forms; it may for example be smooth on one or both sides or have longitudinal grooves and/or transverse grooves and/or depressions suitable for positioning of one or more fingers, or other surface modifications, such as punctiform protrusions, indentations, and the like, which permit slip-free holding.

As explained, the device according to the invention preferably comprises at least one guide element. This guide element may serve as guide for the slot of the extension hollow portion of the grip element or as guide for the support member present. It is however also possible to provide on the surface of the bush simultaneously a guide element for the slit of the extension hollow portion and a guide element for the support member.

As guide element for the support member preferably a guide groove is provided whereas as guide element for the slit, which can extend over the entire length or only a part of the length of the bush, preferably a guide web is provided or one or more punctiform protrusions, indentations, or the like, lying in a row in the longitudinal direction. The guide elements are so formed that they are preferably substantially complementary to the portion of the extension piece which they are to guide.

The preferably provided support member of the extension piece is secured to the grip plate on the side thereof facing the metal cannula extension and when the grip plate element is fitted to the catheter is inserted with the edge face facing the bush on the surface of said bush or into the possibly present guide element in the surface of said bush. The form and size of this guide element which is preferably a guide groove depends on the size and configuration of the edge face of the support member to be inserted into said element and may for example be in the form of a rectangle, square, triangle, or semicircular, or the like, and is preferably positively engageable with the edge of the support member to be inserted. The support member may have any suitable expedient form and size which quarantee that the extension piece is reliably secured on the bush of the catheter. For example, the support member may be in the form of a plate or a body and be shaped in the form of a wedge, a circular segment, a rectangle, a square, a triangle, a triangle with notched base surface, and the like, and is secured to the grip plate in such a manner that said plate is disposed substantially at right-angles, preferably perpendicularly, to the catheter tube or flexible tubing. The support member preferably consists of a wedge-shaped plate.

The extension hollow portion comprises a slit extending over the entire length of the hollow cylinder. This slot may be disposed laterally on the extension hollow piece or at the side thereof opposite the grip plate, i.e. at the bottom side, and is preferably arranged at the bottom side of the extension hollow portion. The width of the slit is such that firstly easy fitting and removal of the extension piece is ensured and secondly falling off or unintentional pulling off of the grip plate from the catheter during handling is avoided. The width of the slit corresponds preferably substantially to the diameter of the catheter tube or tubing or is slightly greater than said diameter.

The extension hollow portion is so formed that it adjoins or fits the outer form of the portion of the bush on which it is placed in positive manner, i.e. is substantially complementary to the outer form of the hollow cylinder and firmly surrounds said portion except for the remaining slit. The extension hollow portion may be cylindrical or conical and is preferably cylindrical. It comprises parallel generatrices extending parallel to the surface of the bush and preferably one or more, at least one, preferably two, conically extending engagement surfaces.

The grip plate extends substantially parallel, preferably exactly parallel, to the grip piece of the metal needle hub or extension.

The extension piece is placed on the catheter by first fitting the extension piece with the slit over the catheter tube or catheter flexible tube, the support member, if present, pointing towards the bush. Thereafter, the extension piece is moved towards the bush until the extension hollow portion firmly engages around the bush and the lower edge of the support member is inserted in the guide groove possibly present on the surface of the bush. Removal is in the opposite order.

In use, the metal needle of the metal needle extension, which preferably has a grip piece, is inserted at the connector into the puncture cannula until it projects with its tip from the end thereof and the securing means on the connector meet and engage in corresponding means on the metal needle extension. Thereafter, this catheter or puncture cannula can be used for puncturing (or catheterizing, for which purpose the two grip plates are gripped simultaneously between thumb and index finger and thus the catheter and metal cannula extension pressed against each other during the puncturing. In this manner a longitudinal displacement of metal needle and puncture cannula relatively to each other is avoided and the handling during the puncturing facilitated, making the puncturing more reliable and safer. After puncturing the puncture cannula is advanced into the vessel or body cavity, the metal needle withdrawn, the catheter introduced, the puncture cannula removed from the body, and in a manner known per se secured by means of plates or wings.

The catheters according to the invention are made from physiologically neutral material usual for catheter production. The extension piece, the bush and the metal needle extension or joining piece, possibly with grip piece, can be made from the same or different material, preferably from the same material. A suitable material is for example polycarbonate.

The catheter according to the invention is suitable both as short-time or indwelling catheter for body cavities and for vessels, preferably as indwelling catheter for vessels, in particular for the catheterizing of the vena basilica, subclavia or jugularis.

Figure 2:
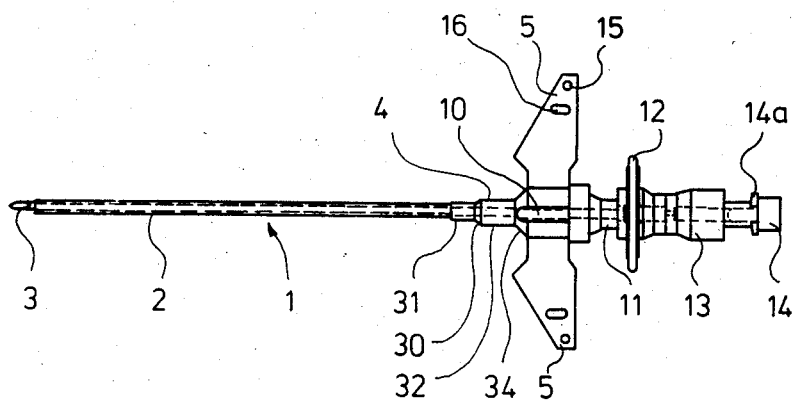
Figure 11:
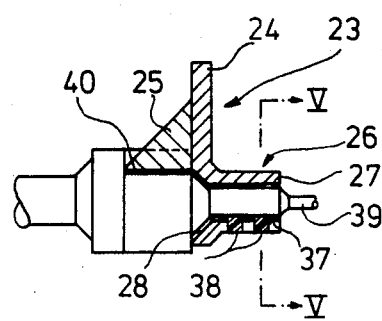
Figure 12:
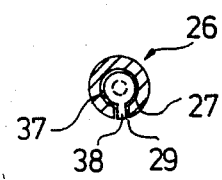

Further details, embodiments and features of the invention will be explained hereinafter with the aid of the drawings, wherein:

FIG. 1 is a side view of an embodiment of the catheter according to the invention with metal needle extension or joining piece, and the puncture cannula according to the invention, FIG. 2 is a plan view of the embodiment of the catheter according to the invention according to FIG. 1 without extension piece, FIG. 3 is a side view of the extension piece according to FIG. 1, FIG. 4 is a section through the extension piece according to FIG. 3 along the line I—I, FIG. 5 is a section through the extension piece according to FIG. 3 along the line II—II, FIG. 6 is a side view of another embodiment of the extension piece, FIG. 7 is a section through the extension piece according to FIG. 6 along the line III—III, FIG. 8 is a section through the extension piece according to FIG. 6 along the line IV—IV, FIG. 9 is side view of another embodiment of the extension piece, FIG. 10 is a side view of a further embodiment of the extension piece, FIG. 11 is a partial section of the extension piece of FIGS. 6–8 and the corresponding bush of the catheter and FIG. 12 is a section along the line V—V of FIG. 11.

In FIGS. 1 and 2 a catheter 1 is shown which comprises substantially a puncture cannula or a catheter tube 2, bush 4, with securing wings or plates 5 disposed laterally on the bush 4 and connected in the usual manner together and to the bush, possibly by a strap or ring firmly encircling the bush, and a detachable extension piece 6. The catheter 1 is connected via the connecting piece 11 of the bush 4 to a metal needle extension or joining piece 13 usual in medical technology and comprising a grip piece 12, by conventional securing means. In FIGS. 1 and 2 reference numeral 3 denotes the metal cannula or needle. The puncture cannula thus illustrated with metal cannula extension or adjoining piece is sealed with a plug 14 but may also be closed with other conventional closure means, such as caps which are secured to the detents 14a which represent part of a screw connection.

The bush or sleeve 4 comprises essentially the actual bush which merges at one end into a tubular continuation 31 via which the puncture cannula 2 is fixedly connected to the bush 4, and at the other end comprises a connector 11 which serves for the connection of supply or transfer appliances, for example an infusion apparatus, further catheters or the metal needle extension. In the interior the bush preferably comprises a valve (not shown) which can be opened by the tip of the metal cannula or needle 3 or of a Luer connecting cone and which prevents body fluid emerging from the catheter in the open condition or air entering.

As apparent from FIG. 2, on the surface the bush 4 has straight, i.e. extending parallel to the catheter tube 2, surfaces 32 and conically beveled surface portions 30, 34. In addition, as apparent from FIG. 2, at the portion of the bush which adjoins the conically beveled surface 34 the surface of the bush 4 comprises a guide groove 10 for the support member 8.

15 and 16 denote the securing holes or slots formed in the plates or wings 5, through which the catheter can be sewn to the skin of the patient. As apparent from FIGS. 1 and 2, the securing plates and wings 5 may advantageously be arranged on the bush 4 in such a manner that when the plates or wings lie on the skin of the patient the catheter extends with its longitudinal axis inclined upwardly, starting from the metal needle tip in the direction towards the connecting piece 11. The angle between the longitudinal axis of the catheter and the plates or wings 5 (lying on the skin of the patient) may advantageously be about 5°–20°, for example about 10°.

The extension piece 6 is shown in FIG. 1 in the manner in which it is advantageously disposed on the bush 4 of the catheter 1. The extension piece 6 comprises the grip plate 7, to which the wedge-shaped support member 8 is secured, and the slit hollow cylindrical extension hollow portion 9; in the extension piece 6 shown in FIG. 1 the slit is disposed at the lower side of the extension hollow piece 9, i.e. not visible. The grip plate 7 is disposed substantially perpendicularly on the bush 4 and extends substantially parallel to the grip piece 12 of the metal needle extension or joining piece 13. The support member can be secured to the grip plate 7 in usual manner, for example by adhering, welding and/or insertion into said grip plate, or the extension piece 6 can be made as an integral body by known techniques, e.g. injection molding, compression molding or the like.

In FIG. 3 detachable extension piece 6 disposed in FIG. 1 on the catheter 1 is shown on its own, the grip plate again being designated by 7, the support member by 8 and the slit extension hollow portion by 9.

In FIG. 4, which illustrates a section along the line I—I of FIG. 3, the parallel generator lines 17, 18 and the conically extending engagement surfaces 19 and 20 of the extension hollow portion 9 can be seen. When the extension piece 6 is fitted onto the bush 4 of the catheter 1 the hollow piece 9 engages with its parallel surface lines 17, 18 the surface 32 of the bush 4 and the conical engagement surfaces 19 and 20 bear on the conically beveled surface portions 30 and 34 of the bush 4.

FIG. 5, which represents a section along the line II—II of FIG. 3, clearly shows the slit 21 disposed at the bottom side of the extension hollow portion 9 and extending over the entire length of the bottom side of said portion 9, passing both through the surface line 18 and the engagement surfaces 19 and 20. According to another embodiment the slit may be disposed laterally on the extension hollow portion 9 and not at the bottom of said portion 9.

In FIGS. 6 to 10 other embodiments of the detachable extension piece according to the invention are shown. FIGS. 6 to 8 show an extension piece 23 which corresponds substantially to that illustrated in FIGS. 3 to 5 with the exception that the slit extension hollow portion 26 comprises only one conically extending engagement surface 28. In FIGS. 6 to 8, 24 denotes the grip plate, 25 the support member, 27 the parallel surface lines and 29 the slit disposed at the lower side of the extension hollow portion 26. When the extension piece 23 is fitted on the bush 4 of the catheter 1 (according to FIG. 2) the parallel surface lines 27 of the extension hollow portion 26 engage round the surface 32 of the bush 4 and the conically extending engagement faces 28 of the hollow portion 26 bear on the conically beveled engagement surfaces 34 of the bush 4 whilst the support member 25 is inserted with its lower edge face into the guide groove 10.

The embodiments of the extension piece illustrated in FIGS. 9 and 10 correspond substantially to the embodiment illustrated in FIG. 3 with the exception that in the embodiments illustrated in FIGS. 9 and 10 the support member has a different convenient form.

According to the embodiment illustrated in FIG. 9 the support member 35 is in the form of a plate-shaped circular segment or section whilst according to the embodiment illustrated in FIG. 10 the support member 36 has the form of a triangular plate and the base of the right-angle triangle thereof is inwardly curved or notched.

FIG. 11 is a partial section through the extension piece 23 and the bush 37 of the catheter whereas FIG. 12 is a section along the line V—V of FIG. 11. The extension hollow portion 26 engages around the bush 37 at the lines 27 and the engagement surfaces 28 except for the slit 29 in which the guide element 38 is disposed in the form of punctiform protuberances. 39 denotes the tubular continuation of the bush 37. 40 denotes the guide groove for the support member 23.

The catheters or puncture cannulas according to the invention may also have an extension piece which consists only of the grip plate 7, 24 and the slit hollow portion, i.e. has no support member. However, in this case the hollow body must be correspondingly dimensioned to guarantee a reliable attachment to the bush and reliable handling of catheter and puncture cannula during the puncturing. For example, the extension hollow portion may be so long that it also engages round the tubular continuation 31 of the bush 4. The slit extension hollow portion may also be guided on the bush by one of the guide elements (for the slit) explained above. However, the use of an extension piece with support member as described above is preferred.

We claim:

1. A device for introducing a catheter into body cavities comprising
    an outer catheter portion and an inner puncture needle portion,
    said catheter portion, rearwardly of the segment thereof to be introduced into said cavities having a bush circumferentially and rigidly disposed thereon,
    said bush comprising a forward and a rearward coaxial segment, the forward segment having a tail portion of forwardly directed frustroconical crossection, said tail portion being located between said forward and said rearward coaxial segments,
    a pair of substantially coplanar wings rigidly disposed on the rearward section of said bush on opposite sides thereof, said wings being so disposed that when said catheter is disposed in the body cavities the said wings will lie on the skin of the patient and be attachable thereto,
    a grip piece rigidly attached to the needle portion disposed rearwardly of the bush, and a grip module comprising an upper grip plate and a lower hollow extension portion,
    said extension portion being dimensioned to engage snugly around the forward segment of the bush, but detachable therefrom, and having a longitudinal slit therein.

2. Device according to claim 1 characterized in that the outer surface of the bush (4, 37) comprises at least one guide element (10, 38, 40) for the extension piece (6, 23).

3. Device according to claim 2 characterized in that the extension piece (6, 23) comprises a support member (8, 25, 35, 36).

4. Device according to claim 3 characterized in that the support member (8, 25) is in the form of a wedge-shaped plate or a circular segment.

5. Device according to claim 2 characterized in that the guide element (10, 40) is a guide groove.

6. Device according to claim 5 characterized in that the guide groove (10) for the support member (8, 25, 35, 36) on the bush (4) is made rectangular.

7. Device according to claim 1 characterized in that the surface of the bush (4, 37) comprises a guide element (38) for the slit (21, 29) of the hollow portion (9, 26).

8. Device according to claim 7, characterized in that the guide element (38) extends over part or all of the length of the bush (4, 37) and is in the form of a guide web, punctiform protuberances or indentations.

9. Device according to claim 1 characterized in that the extension hollow portion (9, 26) of the extension piece (6, 23) comprises generating or surface lines (17, 18) extending parallel to the surfaces (32) of the bush (4) and conically extending and inclined surfaces (19, 20) bearing on the beveled surface portion (30, 34) of the bush (4).

10. Device according to claim 9 characterized in that the extension hollow portion (9, 26) of the extension piece (6, 23) comprises surface lines (27) extending parallel to the surfaces (32) of the bush (4) and a conically extending engagement surface (28) bearing on the inclined surface (34) of the bush (4).

11. Device according to claim 1 characterized in that the slit (21, 29) is disposed at the lower side of the extension hollow portion (9, 26) or laterally on the hollow portion (9, 26).

12. Device according to claim 1 characterized in that the grip plate (7, 27) of the extension piece (6, 23) is provided at least on one side with longitudinal grooves or transverse grooves.

13. Device according to claim 1 characterized in that the grip plate (7, 24) of the extension piece (6, 23) is provided on at least one side with depressions for placing or inserting at least one finger.

14. Device according to claim 1 characterized in that the grip plate (7, 24) of the grip plate element (6, 23) is disposed perpendicularly to the catheter tube (2).

15. Device according to claim 1 characterized in that the grip plate (7, 24) of the extension piece (6, 23) is disposed parallel to the grip piece (12) of the metal needle extension or joining piece (13).

16. A device in accordance with claim 1 wherein said bush additionally comprises a middle segment of substantially cylindrical cross section disposed forward of said frustroconical tail portion.

17. A device in accordance with claim 16 wherein said bush additionally comprises a forward segment of frustruconical cross section disposed forward of said cylindrical middle segment.

18. A device of claim 16 wherein said extension portion is additionally provided with a hollow, slit, forward portion of substantially cylindrical crosssection.

19. A device of claim 18 wherein said extension portion is additionally provided with a further hollow, slit, forward portion of forwardly directed, substantially frustroconical crosssection located forwardly of said cylindrical cross sectioned portion.

20. A device of claim 1 further comprising a groove in said rearward section of said bush and a support member attached to said extension portion engageable in said groove.

21. A grip module comprising an upper grip plate and a lower hollow extension portion and a support member attached to said extension portion,
for use with a device for introducing a catheter into body cavities comprising an outer catheter portion and an inner puncture needle portion,
said catheter portion, rearwardly of the segment thereof to be introduced into said cavities having a bush circumferentially and rigidly disposed thereon,
said bush comprising a forward and a rearward coaxial segment having a groove in the latter, the forward segment having a tail portion of forwardly directed frustroconical cross section, said tail portion being located forward of said rearward coaxial segments, said needle portion being disposed in and coaxial with said bush and said catheter portion,
a pair of substantially coplanar wings rigidly disposed on the rearward section of said bush on opposite sides thereof, said wings being so disposed that when said catheter is disposed in the body cavity the said wings will lie on the skin of the patient and be attachable thereto and
a grip piece rigidly attached to the needle portion disposed rearwardly of the bush,
said support member attached to said extension portion being engageable in said groove in said rearward segment said extension portion being dimensioned to engage snugly around the forward segment of the bush, but detachable therefrom, and having a longitudinal slit therein.

22. A grip module comprising an upper grip plate and a lower hollow extension portion, for use with a device for introducing a catheter into body cavities comprising an outer catheter portion and an inner puncture needle portion,
said extension portion having a longitudinal slit therein and comprising a body segment and a rearward segment coaxial therewith,
said body segment having a substantially cylindrical cross section,
said rearward segment having a forwardly directed frustroconical cross section, the internal diameter of the forward end of said segment being the same as that of the body segment.
said upper grip plate being located on and attached to the outer surface part of said extension portion substantially opposite to the part of the outer surface having the slit therein.

23. A grip module according to claim 22, additionally comprising a forward segment of a forwardly directed frustroconical cross section disposed forwardly of said cylindrical body portion, the internal diameter of the rearward end of said forward segment being equal to that of the internal diameter of the said main body portion.

* * * * *